United States Patent
Imai et al.

(10) Patent No.: US 10,481,028 B2
(45) Date of Patent: Nov. 19, 2019

(54) PRESSURE DETECTION DEVICE

(71) Applicant: Surpass Industry Co., Ltd., Saitama (JP)

(72) Inventors: Hiroshi Imai, Saitama (JP); Masamichi Kobayashi, Saitama (JP)

(73) Assignee: Surpass Industry Co., Ltd., Saitama (JP)

( * ) Notice: Subject to any disclaimer, the term of this patent is extended or adjusted under 35 U.S.C. 154(b) by 2 days.

(21) Appl. No.: 15/900,163

(22) Filed: Feb. 20, 2018

(65) Prior Publication Data
US 2018/0238761 A1    Aug. 23, 2018

(30) Foreign Application Priority Data
Feb. 22, 2017    (JP) .................... 2017-031290

(51) Int. Cl.
*G01L 13/02*    (2006.01)
*G01L 19/00*    (2006.01)
(Continued)

(52) U.S. Cl.
CPC ....... *G01L 19/0023* (2013.01); *A61M 1/3641* (2014.02); *G01L 9/0051* (2013.01); *G01L 9/0055* (2013.01); *G01L 13/025* (2013.01); *G01L 19/003* (2013.01); *G01L 19/0645* (2013.01); *G01L 19/144* (2013.01)

(58) Field of Classification Search
CPC .. G01L 13/026; A61M 1/3641; A61M 1/3639
See application file for complete search history.

(56) References Cited

U.S. PATENT DOCUMENTS 6,280,406 B1    8/2001    Dolecek et al.
8,156,817 B2    4/2012    Kaneko et al.
(Continued)

FOREIGN PATENT DOCUMENTS

EP    2000790 A1    12/2008
EP    2404149 A1    1/2012
(Continued)

OTHER PUBLICATIONS

Extended European Search Report dated Jul. 12, 2018 in corresponding application 18157429.4.

*Primary Examiner* — Herbert K Roberts
(74) *Attorney, Agent, or Firm* — Muncy, Geissler, Olds & Lowe, P.C.

(57) ABSTRACT

Provided is a pressure detection device which includes a pressure detection unit and a flow passage unit. The pressure detection unit includes a pressure sensor including a diaphragm and a first connection portion joined to the diaphragm. The flow passage unit includes a diaphragm and a second connection portion joined to the diaphragm. One of the first connection portion and the second connection portion is formed of a magnet, and the other of the first connection portion and the second connection portion is formed of a magnet or a magnetic body. In a state where the flow passage unit is mounted on the pressure detection unit, the first connection portion and the second connection portion are disposed in a state where the first connection portion and the second connection portion are attracted to each other by a magnetic force.

9 Claims, 12 Drawing Sheets

(51) Int. Cl.
*A61M 1/36* (2006.01)
*G01L 9/00* (2006.01)
*G01L 19/06* (2006.01)
*G01L 19/14* (2006.01)

(56) References Cited

U.S. PATENT DOCUMENTS

| | | |
|---|---|---|
| 8,307,712 B2 | 11/2012 | Popp |
| 8,495,916 B2 | 7/2013 | Popp |
| 8,511,167 B2 | 8/2013 | Popp |
| 8,528,410 B2 | 9/2013 | Popp |
| 8,528,412 B2 | 9/2013 | Popp |
| 9,551,625 B2 | 1/2017 | Brugger et al. |
| 9,835,509 B2 | 12/2017 | Brugger et al. |
| 2005/0160828 A1 | 7/2005 | Hasunuma |
| 2013/0205907 A1* | 8/2013 | Fukano ............... G01L 7/08 73/715 |
| 2014/0076058 A1* | 3/2014 | Brugger ............ G01L 9/0041 73/723 |
| 2015/0260601 A1* | 9/2015 | Hasunuma ......... G01L 19/0092 73/714 |
| 2018/0128698 A1 | 5/2018 | Brugger et al. |

FOREIGN PATENT DOCUMENTS

| | | |
|---|---|---|
| JP | 2005-207946 A | 8/2005 |
| WO | WO2010/102008 A1 | 9/2010 |
| WO | WO2012166980 A2 | 12/2012 |

\* cited by examiner

PRESSURE DETECTION DEVICE

CROSS-REFERENCE TO RELATED APPLICATIONS

This application is based on Japanese Patent Application No. 2017-031290, the contents of which are incorporated herein by reference in its entirety.

TECHNICAL FIELD

The present invention relates to a pressure detection device which detects a pressure of a fluid flowing through a flow passage.

BACKGROUND ART

Conventionally, there is known an inline pressure sensor where a body and a sensor body are formed into one integral body, wherein a flow passage, through which a liquid such as a liquid medicine is made to flow, is formed in the body, and the sensor body detects a pressure of the liquid which is transmitted to a pressure receiving surface through a protective sheet (see Japanese Unexamined Patent Application, Publication No. 2005-207946 (hereinafter referred to as Patent Literature 1), for example).

The pressure sensor disclosed in Patent Literature 1 is configured to detect a pressure of a fluid which is transmitted to the sensor body through the protective sheet mounted on a lower surface of the sensor body.

SUMMARY

Technical Problem

The pressure sensor disclosed in Patent Literature 1 can acquire a detection value, which corresponds to a pressure at which a fluid presses the protective sheet, when the protective sheet is pressed to the lower surface of the sensor body by the pressure of the fluid.

However, the pressure sensor disclosed in Patent Literature 1 cannot acquire a detection value which corresponds to a pressure (negative pressure) of a fluid when the pressure of the fluid lowers so that the protective sheet receives a force by which the protective sheet is separated from the lower surface of the sensor body. This is because the pressure sensor disclosed in Patent Literature 1 is an electrostatic capacitance type pressure sensor or a piezoelectric type pressure sensor which acquires, as a detection value, a force by which the lower surface of the sensor body is pressed. Accordingly, the pressure sensor disclosed in Patent Literature 1 cannot detect a pressure of a fluid with accuracy when the pressure of the fluid is a negative pressure.

Further, in the pressure sensor disclosed in Patent Literature 1, the body in which the flow passage is formed and the sensor body are formed into one integral body. Accordingly, in changing a liquid forming a detection target, it is necessary to wash the existing flow passage with pure water or the like.

However, it is difficult to completely remove a liquid remaining in the flow passage with the method of washing the flow passage and, at the same time, such a method requires a lot of time for performing a washing operation. Accordingly, for example, in a medical field, a biotechnology field or the like which requires a flow passage where the inside of the flow passage is sterilized or the like thus being completely clean, the method of washing the flow passage in changing a liquid is not sufficient in view of smoothness and safety of operation.

The present disclosure has been made under such circumstances, and it is an object of the present disclosure to provide a pressure detection device where smoothness and safety of operation of changing a fluid to be introduced into a flow passage are enhanced, and a pressure of a fluid can be detected with accuracy even when the pressure of the fluid is a negative pressure.

Solution to Problem

To solve the above-mentioned problem, the present disclosure adopts the following solutions.

A pressure detection device includes: a pressure detection unit configured to detect a pressure transmitted to a pressure detecting portion; a flow passage unit in which a flow passage for introducing a fluid is formed; and a mounting mechanism configured to detachably mount the flow passage unit on the pressure detection unit. The pressure detection unit includes: a pressure sensor including the pressure detecting portion; and a first connection portion joined to the pressure detecting portion. The flow passage unit includes: a pressure receiving portion configured to be displaced by receiving a pressure of the fluid flowing through the flow passage; and a second connection portion joined to the pressure receiving portion. One of the first connection portion and the second connection portion is formed of a magnet, and the other of the first connection portion and the second connection portion is formed of a magnet or a magnetic body. In a state where the flow passage unit is mounted on the pressure detection unit by the mounting mechanism, the first connection portion and the second connection portion are disposed in a state where the first connection portion and the second connection portion are attracted to each other by a magnetic force.

According to the pressure detection device of one aspect of the present disclosure, the flow passage unit is detachably mounted on the pressure detection unit by the mounting mechanism. Accordingly, to change a fluid to be introduced into the flow passage, the flow passage unit which is already used is removed from the pressure detection unit, and a flow passage unit which is unused can be newly mounted on the pressure detection unit.

With such a configuration, in changing a fluid to be introduced into the flow passage, it becomes unnecessary to perform a washing operation of the flow passage, which requires a lot of time, so that smoothness of the operation can be improved. Further, a flow passage unit which is unused can be newly used and hence, safety can be improved.

Further, according to the pressure detection device of one aspect of the present disclosure, in a state where the flow passage unit is mounted on the pressure detection unit by the mounting mechanism, the first connection portion joined to the pressure detecting portion and the second connection portion joined to the pressure receiving portion are disposed in a state where the connection portions are attracted to each other by a magnetic force. Accordingly, when a pressure of a fluid flowing through the flow passage is a positive pressure, the second connection portion joined to the pressure receiving portion is separated from the flow passage side due to the pressure of the fluid, and the second connection portion presses the first connection portion to the pressure detecting portion. With such pressing, the pressure of the fluid is detected as a positive pressure by the pressure detecting portion.

On the other hand, when a pressure of a fluid flowing through the flow passage is a negative pressure, the second connection portion joined to the pressure receiving portion is attracted to the flow passage side due to the pressure of the fluid, and the second connection portion attracts the first connection portion, which is connected to the second connection portion by a magnetic force, to the flow passage side. With such attraction, the pressure of the fluid is detected as a negative pressure by the pressure detecting portion.

As described above, according to the pressure detection device of one aspect of the present disclosure, it is possible to provide a pressure detection device where smoothness and safety of an operation of changing a fluid to be introduced into the flow passage are improved, and a pressure of a fluid can be detected with accuracy even when the pressure of the fluid is a negative pressure.

In the pressure detection device according to one aspect of the present disclosure, the first connection portion may be formed of a magnet, and the second connection portion may be formed of a magnetic body.

The flow passage unit, which is exchanged after being used, is formed of a magnetic body, which is relatively cheap. Accordingly, running cost can be reduced when the pressure detection device is continuously used.

In the pressure detection device according to one aspect of the present disclosure, an end surface of the first connection portion on a side of the flow passage unit may be formed to have a planar shape, and an end surface of the second connection portion on a side of the pressure detection unit may be formed to have a spherical shape which projects toward the first connection portion.

With such a configuration, the first connection portion and the second connection portion are connected with each other only at one point of a spherical distal end of the first connection portion. Accordingly, a position where a pressure is transmitted between the first connection portion and the second connection portion is fixed to one point. Therefore, it is possible to prevent a problem that a position where a pressure is transmitted between the first connection portion and the second connection portion changes so that an error occurs in pressure detection value.

In the pressure detection device according to one aspect of the present disclosure, the second connection portion may be disposed in an inner space defined by the pressure receiving portion and the pressure detecting portion, the first connection portion may be joined to a surface of the pressure detecting portion which is not in contact with the inner space, and in a state where the flow passage unit is mounted on the pressure detection unit by the mounting mechanism, the first connection portion and the second connection portion may be disposed in a state where the first connection portion and the second connection portion are attracted to each other by a magnetic force with the pressure detecting portion interposed between the first connection portion and the second connection portion.

According to the pressure detection device having such a configuration, the first connection portion is joined to a surface of the pressure detecting portion on the side which is not in contact with the inner space. With such a configuration, in removing the flow passage unit from the pressure detection unit, a magnetic force in the direction that the first connection portion approaches the pressure detecting portion acts on a portion where the first connection portion and the pressure detecting portion are joined to each other.

Accordingly, compared to the case where the first connection portion is joined to a surface of the pressure detecting portion on the side which is in contact with the inner space, it is possible to prevent, by the action of a magnetic force, a problem that the first connection portion is peeled off from the pressure detecting portion. Further, there is no possibility that a manipulator inadvertently comes into contact with the portion where the first connection portion and the pressure detecting portion are joined to each other. Accordingly, it is possible to prevent a problem that the first connection portion is peeled off from the pressure detecting portion due to carelessness of the manipulator.

In the pressure detection device according to one aspect of the present disclosure, the pressure detection unit may have a communication flow passage configured to make the inner space defined by the pressure receiving portion formed into a film shape and the pressure detecting portion formed into a film shape and an outer space maintained at an atmospheric pressure communicate with each other.

With such a configuration, the inner space defined by the pressure receiving portion of the flow passage unit and the pressure detecting portion of the pressure detection unit is maintained at an atmospheric pressure. Accordingly, the pressure detecting portion can detect a pressure of a fluid with accuracy.

Advantageous Effects

According to the present disclosure, it is possible to provide a pressure detection device where smoothness and safety of operation of changing a fluid to be introduced into a flow passage are enhanced, and a pressure of a fluid can be detected with accuracy even when the pressure of the fluid is a negative pressure.

DESCRIPTION OF EMBODIMENTS

First Embodiment

Hereinafter, a pressure detection device 100 according to a first embodiment of the present disclosure is described with reference to drawings.

Figure 1:
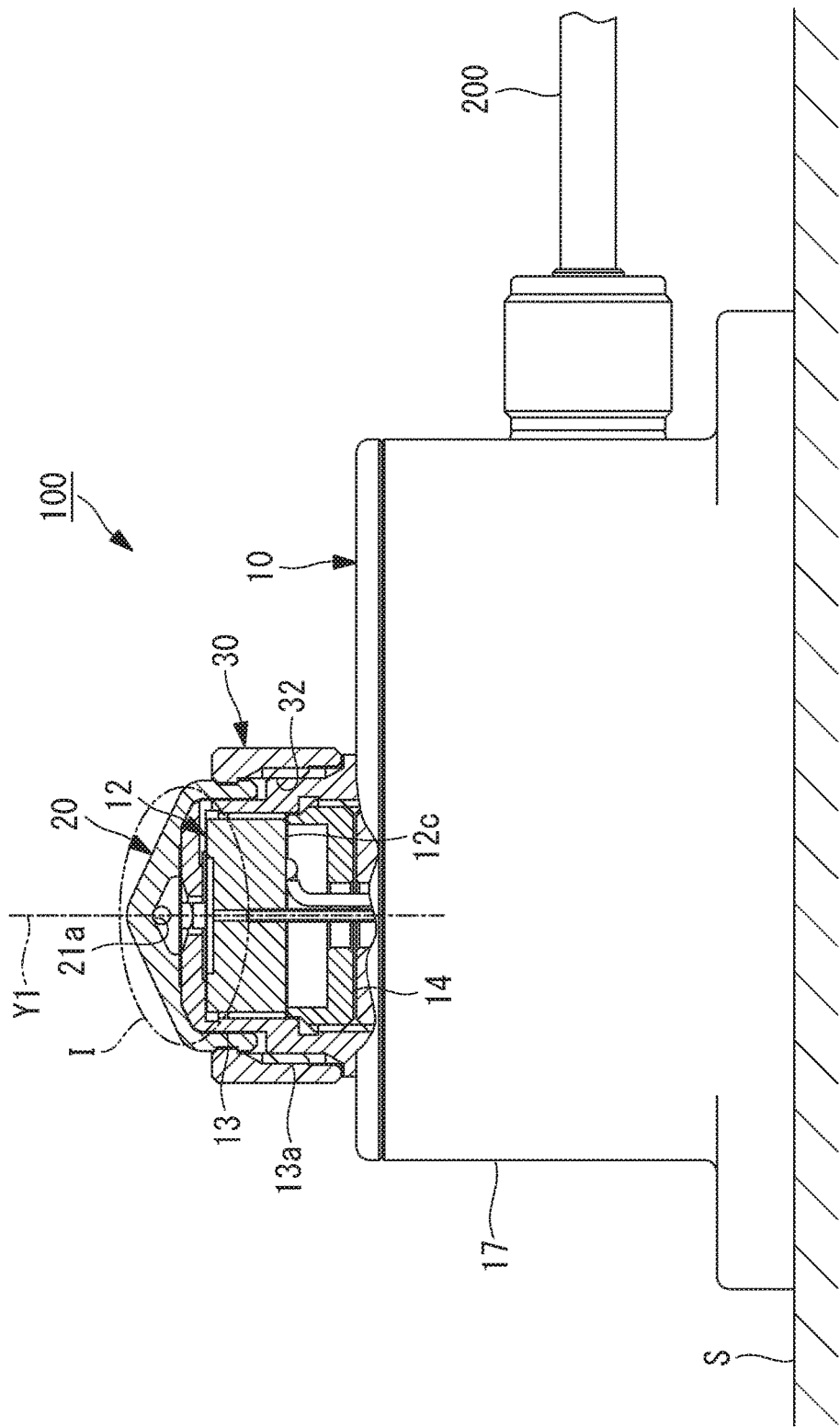
FIG. 1 is a partial longitudinal cross-sectional view showing a pressure detection device of a first embodiment.

As shown in FIG. 1, the pressure detection device 100 of this embodiment includes: a pressure detection unit 10 mounted on an installation surface S by fastening bolts (not shown in the drawing); a flow passage unit 20 in which a flow passage 21a is formed; and a nut 30 (mounting mechanism) for detachably mounting the flow passage unit 20 on the pressure detection unit 10.

As shown in FIG. 1, the pressure detection unit 10 is mounted on the installation surface S, and the flow passage unit 20 is mounted on the pressure detection unit 10 by the nut 30. The pressure detection device 100 is mounted on the installation surface S in a state where the flow passage unit 20 is mounted on the pressure detection unit 10 by the nut 30 thus forming an integral body.

Next, the pressure detection unit 10 is described in detail. The pressure detection unit 10 is a device which detects a pressure transmitted to a diaphragm 12a. The pressure detection unit 10 includes: a first connection portion 11; a pressure sensor 12; a body portion 13 for accommodating the pressure sensor 12; a sensor holding portion 14 for holding the pressure sensor 12 in a state where the pressure sensor 12 is disposed in the body portion 13; a sensor board (not shown in the drawing) for transmitting power and an electric signal between the pressure sensor 12 and a cable 200; and a housing 17 for accommodating the sensor board. The cable 200 electrically connects the sensor board and a control device disposed outside the pressure detection device 100 with each other.

Figure 3:
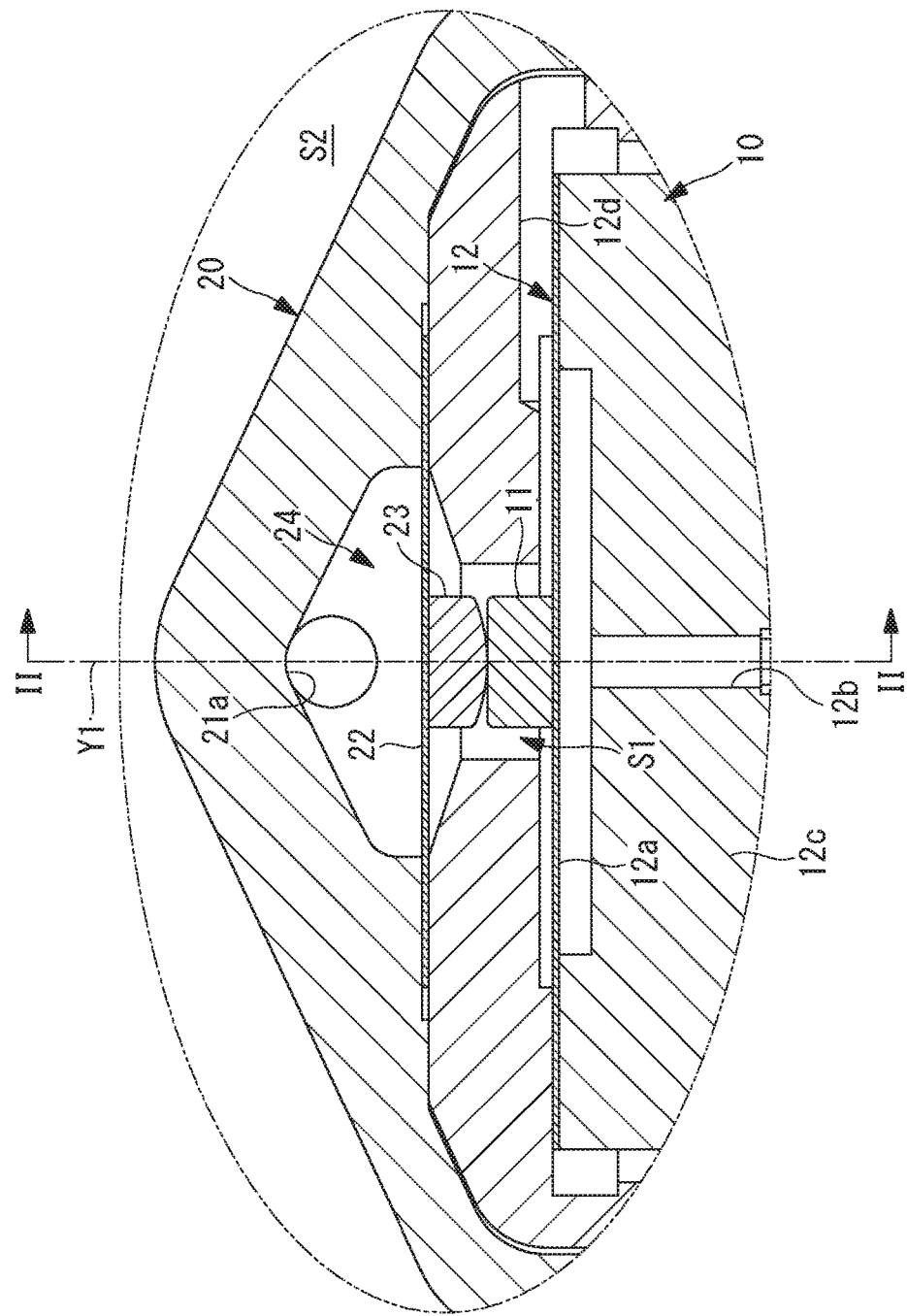
FIG. 3 is a partially enlarged view of a portion I of the pressure detection device shown in FIG. 1.

The first connection portion 11 is formed of a permanent magnet formed into a cylindrical shape along an axis Y1. The first connection portion 11 is made of neodymium or the like, for example. The first connection portion 11 is joined to the diaphragm 12a of the pressure sensor 12 by an adhesive agent (epoxy resin based adhesive agent, for example). As shown in FIG. 3, an end surface of the first connection portion 11 on the flow passage unit 20 side is formed to have a planar shape disposed on a plane which is orthogonal to the axis Y1. The first connection portion 11 attracts a second connection portion 23, which is formed of a magnetic body, by a magnetic force of the permanent magnet, and the first connection portion 11 maintains a state where the first connection portion 11 is in contact with the second connection portion 23. The second connection portion 23, which the flow passage unit 20 includes, is described later.

In the description made heretofore, the first connection portion 11 is formed of a permanent magnet, and the second connection portion 23 is formed of a magnetic body. However, another mode may be adopted. For example, each of both the first connection portion 11 and the second connection portion 23 may be formed of a permanent magnet. Alternatively, the first connection portion 11 may be formed of a magnetic body, and the second connection portion 23 may be formed of a permanent magnet. As described above, in the pressure detection device 100 of this embodiment, one of the first connection portion 11 and the second connection portion 23 is formed of a magnet, and the other of the first connection portion 11 and the second connection portion 23 is formed of a magnet or a magnetic body.

Hereinafter, an example is described where the first connection portion 11 is formed of a permanent magnet, and the second connection portion 23 is formed of a magnetic body.

As shown in FIG. 3 (a partially enlarged view of a portion I in FIG. 1), the pressure sensor 12 includes: the diaphragm 12a (pressure detection surface) formed into a thin film shape using a material having corrosion resistance (for example, sapphire); a strain resistance (not shown in the drawing) adhered to the diaphragm 12a; and a base portion 12c which holds the diaphragm 12a.

The pressure sensor 12 is a strain type sensor. The strain type sensor outputs a pressure signal which corresponds to a change in resistance value of the strain resistance which deforms corresponding to a pressure transmitted to the diaphragm 12a. A through hole 12b, which communicates with the diaphragm 12a, is formed in the base portion 12c so that one surface (a surface on the lower side in FIG. 3) of the diaphragm 12a is maintained at an atmospheric pressure. Accordingly, the pressure sensor 12 is a sensor which detects a gauge pressure using an atmospheric pressure as a reference.

The body portion 13 is a member which accommodates the pressure sensor 12 therein, and on which the flow passage unit 20 is mounted by the nut 30. The body portion 13 is made of a metal material such as SUS304, for example. As shown in FIG. 3, a communication flow passage 12d is formed in the body portion 13. The communication flow passage 12d allows an inner space S1 and an outer space S2 to communicate with each other. The inner space S1 is defined by a diaphragm 22 which the flow passage unit 20 includes and the diaphragm 12a which the pressure sensor 12 includes. The outer space S2 is maintained at an atmospheric pressure.

Figure 2:
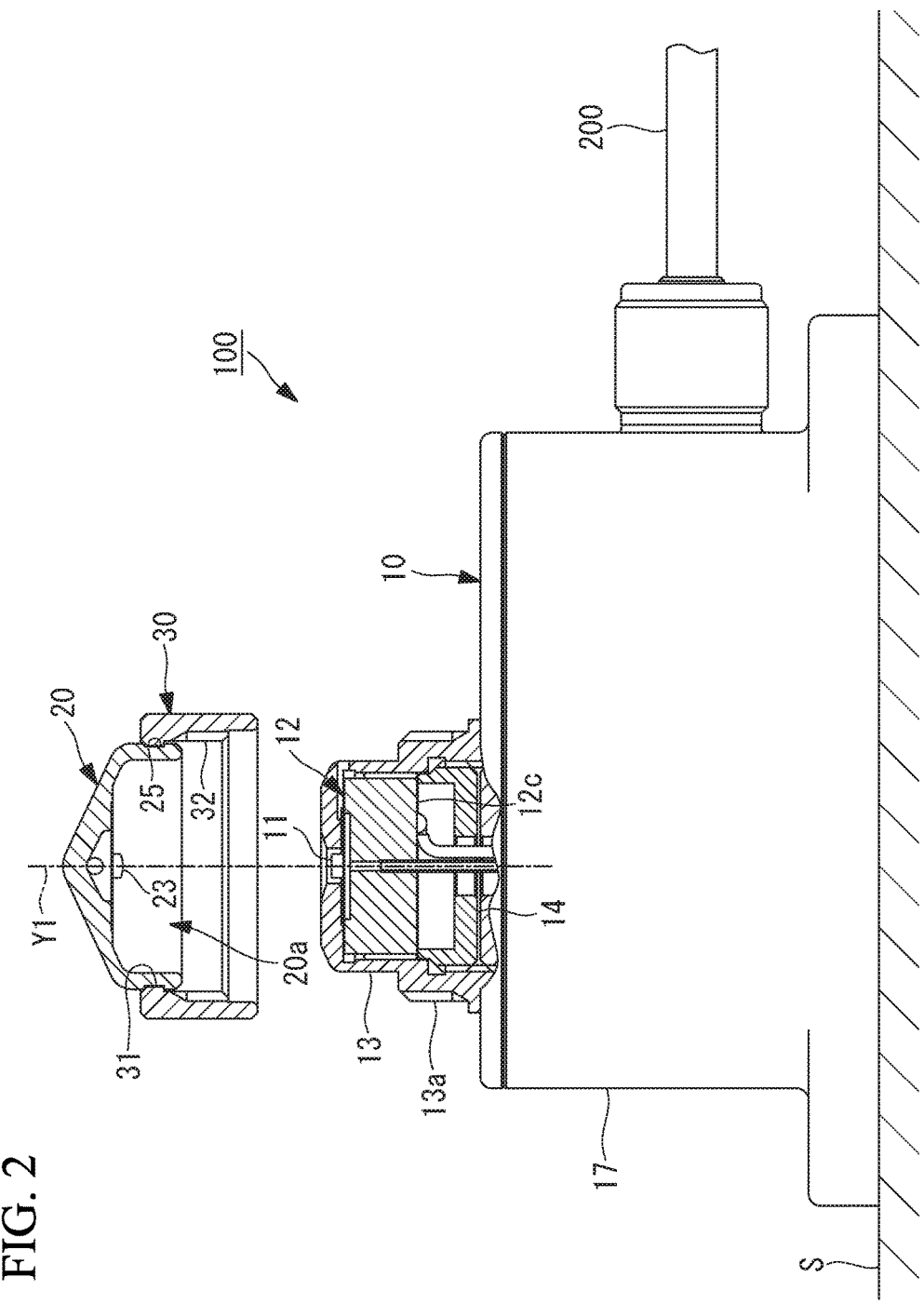
FIG. 2 is a partial longitudinal cross-sectional view showing the pressure detection device where a flow passage unit is removed from a pressure detection unit.

As shown in FIG. 1 and FIG. 2, the sensor holding portion 14 is a member which is formed into a cylindrical shape about an axis Y1 (first axis), and male threads are formed on an outer peripheral surface of the sensor holding portion 14. In a state where the pressure sensor 12 is disposed in an inner peripheral side of the body portion 13, the male threads formed on the outer peripheral surface of the sensor holding portion 14 are fastened to female threads formed on an inner peripheral surface of the body portion 13 so that the sensor holding portion 14 holds the pressure sensor 12 in the body portion 13.

The sensor board (not shown in the drawing) includes: an amplifier circuit (not shown in the drawing) for amplifying a pressure signal outputted by the pressure sensor 12; an interface circuit for transmitting the pressure signal, which is amplified by the amplifier circuit, to a pressure signal line (not shown in the drawing) of the cable 200; a power supply circuit (not shown in the drawing) for transmitting a power supply voltage supplied from the outside through the cable 200 to the pressure sensor 12; a zero-point adjustment circuit (not shown in the drawing) for performing a zero-point adjustment when a zero-point adjustment switch (not shown in the drawing) is pressed and the like.

The zero-point adjustment circuit is a circuit which performs an adjustment such that, when the zero-point adjustment switch (not shown in the drawing) is pressed by a manipulator, a pressure signal to be outputted by the pressure sensor 12 at the point is set as an initial value (zero).

Next, the flow passage unit 20 is described in detail.

Figure 4:
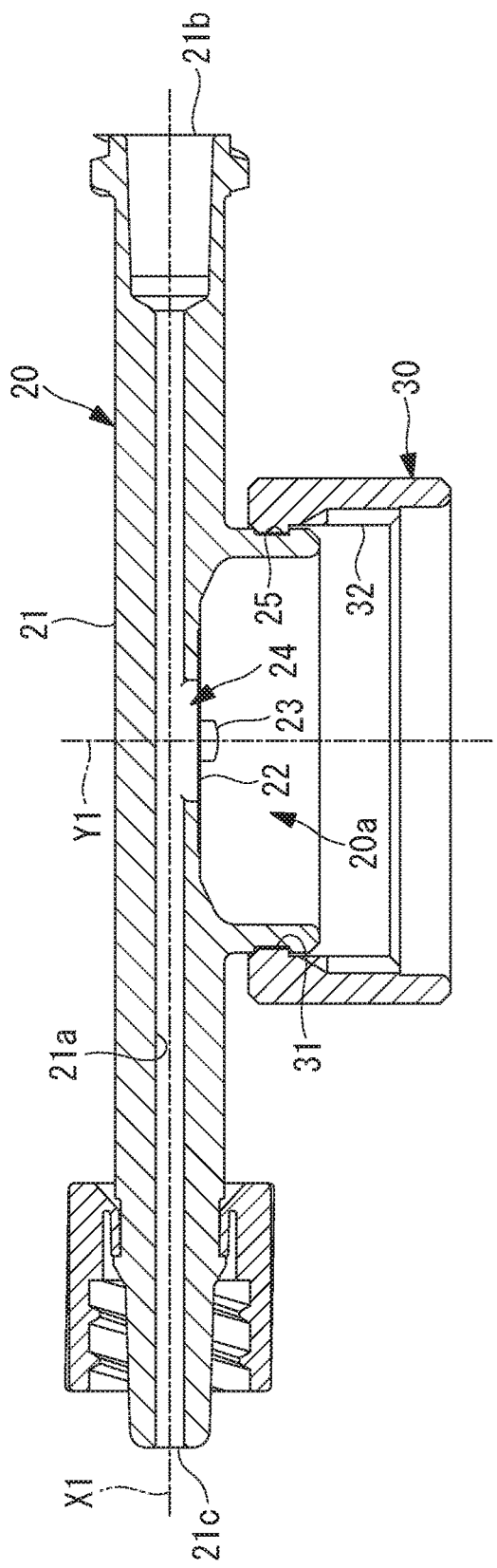
FIG. 4 is a cross-sectional view of the flow passage unit and a nut shown in FIG. 3 as viewed from an arrow II-II.
Figure 5:
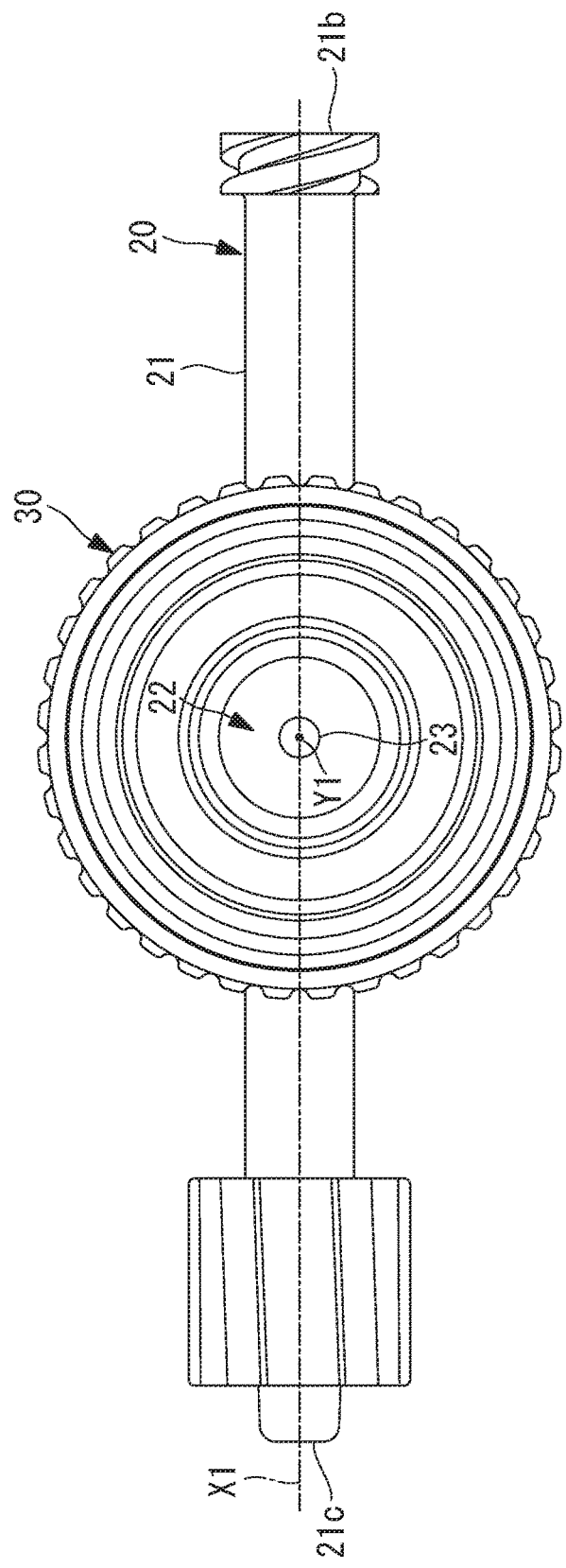
FIG. 5 is a bottom view of the flow passage unit and the nut shown in FIG. 4.

As shown in FIG. 3 to FIG. 5, the flow passage unit 20 includes a flow passage body 21, the diaphragm (pressure receiving portion) 22, and the second connection portion 23.

In this embodiment, FIG. 4 is a cross-sectional view of the flow passage unit 20 and the nut 30 shown in FIG. 3 as viewed from an arrow II-II. Further, FIG. 5 is a bottom view of the flow passage unit 20 and the nut 30 shown in FIG. 4 as viewed from below.

The flow passage body 21 is a member where the flow passage 21a is formed therein. A fluid is made to flow through the flow passage 21a in the flow direction extending along an axis X1 from an inflow port 21b to an outflow port 21c. The flow passage body 21 is made of polycarbonate, for example. A fluid chamber 24, which opens to an area below the flow passage unit 20, is formed at a substantially center position of the flow passage body 21 in the direction of the axis X1. The fluid chamber 24 is a space having a circular cross section, which is orthogonal to the axis Y1. The fluid chamber 24 forms a portion of the flow passage 21a.

An inflow side pipe (not shown in the drawing), through which a fluid is made to flow in the inflow port 21b, is mounted on the inflow port 21b of the flow passage body 21. An outflow side pipe (not shown in the drawing), through which the fluid flowing out from the outflow port 21c flows, is mounted on the outflow port 21c of the flow passage unit 20. A pressure of a fluid flowing through the flow passage 21a from the inflow port 21b to the outflow port 21c is detected by the pressure detection unit 10.

In this embodiment, a fluid means a liquid such as a culture solution, blood or a dialysate, for example. The flow passage unit 20 can be easily mounted on and removed from the pressure detection unit 10 by the nut 30 described later. Accordingly, the pressure detection device 100 of this embodiment is not provided with a mechanism for washing the flow passage 21a, and the flow passage unit 20, which includes the flow passage 21a, can be exchanged at a suitable timing. The pressure detection device 100 having such a configuration is effectively used particularly in a medical field, a biotechnology field or the like which requires a flow passage where the inside of the flow passage is sterilized or the like thus being completely clean.

Further, in FIG. 4, a fluid flows in from the inflow port 21b, and the fluid flows out from the outflow port 21c. However, another mode may be adopted. For example, the direction along which a fluid flows may be reversed by using the inflow port 21b shown in FIG. 4 as an outflow port and by using the outflow port 21c shown in FIG. 4 as an inflow port. Alternatively, it may be possible to adopt the configuration where either one of the inflow port 21b or the outflow port 21c is closed, and a pressure of a fluid introduced into the flow passage 21a having a closed terminal end is detected.

The diaphragm 22 is a member which is formed into a thin film shape using a material having corrosion resistance (for example, a silicone resin material, or polycarbonate). The diaphragm 22 is a member formed into a circular shape as viewed in a plan view using the axis Y1 as a center axis. The diaphragm 22 is joined to a lower surface of the flow passage body 21 by bonding or by welding. Accordingly, there is no possibility that a fluid introduced into the fluid chamber 24 flows out to the outside from the fluid chamber 24. The diaphragm 22 is formed into a thin film shape so that the diaphragm 22 is displaced in the direction of the axis Y1 by receiving a pressure of a fluid flowing through the fluid chamber 24 forming the portion of the flow passage 21a.

The second connection portion 23 is formed of a magnetic body formed into a cylindrical shape along the axis Y1, and is made of an iron material such as S45C stipulated in the JIS standard. The second connection portion 23 is joined to a surface of the diaphragm 22 on the pressure detection unit 10 side by an adhesive agent (for example, epoxy resin based adhesive agent). As shown in FIG. 3, an end surface of the second connection portion 23 on the pressure detection unit 10 side is formed into a spherical shape which projects toward the first connection portion 11 along the axis Y1. The second connection portion 23 is attracted by a magnetic force of the first connection portion 11 formed of a permanent magnet, and the second connection portion 23 is maintained in a state where the second connection portion 23 is in contact with the first connection portion 11.

Next, the description is made with respect to a mechanism for mounting the flow passage unit 20 on the pressure detection unit 10 using the nut 30.

As shown in FIG. 2 and FIG. 4, the nut 30 is a member formed into a cylindrical shape along the axis Y1. An endless annular projecting portion 31, which extends about the axis Y1, is formed on an inner peripheral surface of the nut 30. On the other hand, an endless annular groove portion 25, which extends about the axis Y1, is formed on a portion of an outer peripheral surface of the flow passage unit 20 on the lower end side. The nut 30 is made of an elastically deformable material (for example, resin material). The nut 30 is fitted by pressing on the portion of the outer peripheral surface of the flow passage unit 20 on the lower end side so that the annular projecting portion 31 is engaged with the annular groove portion 25.

As shown in FIG. 2 and FIG. 4, in a state where the annular projecting portion 31 is engaged with the annular groove portion 25, an extremely small gap is formed between an inner peripheral surface of the annular projecting portion 31 and an outer peripheral surface of the annular groove portion 25. Accordingly, in a state where the nut 30 is mounted on the flow passage unit 20, the nut 30 is rotatable about the axis Y1 with respect to the flow passage body 21. With such a configuration, an operator can rotate the nut 30 about the axis Y1 in a state where the operator holds the flow passage unit 20.

In mounting the flow passage unit 20 on the pressure detection unit 10 installed to the installation surface S, the operator performs the operation with the following procedure.

First, as shown in FIG. 2, the flow passage unit 20 is disposed such that a center axis of the flow passage unit 20 agrees with the axis Y1 which is a center axis of the pressure detection unit 10. Then, the flow passage unit 20 is moved downward along the axis Y1 so that the body portion 13 is inserted into a recessed portion 20a formed at a lower portion of the flow passage unit 20.

Next, the operator rotates the nut 30 about the axis Y1 in the fastening direction while gripping the flow passage unit 20. With such operations, female threads 32 formed on the inner peripheral surface of the nut 30 are fastened to male threads 13a formed on an outer peripheral surface of the body portion 13. By fastening the female threads 32 of the nut 30 and the male threads 13a of the pressure detection unit 10 to each other, the second connection portion 23 of the flow passage unit 20 gradually approaches and comes into contact with the first connection portion 11 of the pressure detection unit 10. Accordingly, a state shown in FIG. 1 and FIG. 3 is brought about. The flow passage unit 20 is mounted on the pressure detection unit 10 as described above.

The procedure for mounting the flow passage unit 20 which is unused on the pressure detection unit 10 has been described heretofore. A procedure for removing the flow passage unit 20 which is already used from the pressure detection unit 10 is opposite to the procedure described above.

The operator rotates the nut 30 about the axis Y1 in the fastening release direction while gripping the flow passage unit 20 in a state shown in FIG. 1. With such an operation, fastening between the female threads 32 of the nut 30 and the male threads 13a of the pressure detection unit 10 is released.

In the pressure detection device 100 of this embodiment, the first connection portion 11 joined to the diaphragm 12a and the second connection portion 23 joined to the diaphragm 22 are brought into contact with each other by fastening the female threads 32 of the nut 30 and the male threads 13a of the pressure detection unit 10 to each other. Accordingly, it is possible to prevent that the first connection portion 11 and the second connection portion 23 inadvertently come into contact with each other thus damaging the diaphragm 12a and the diaphragm 22.

As shown in FIG. 1 and FIG. 3, in the pressure detection device 100 of this embodiment, in a state where the flow passage unit 20 is mounted on the pressure detection unit 10 by the nut 30, the second connection portion 23 formed of a magnetic body is attracted by and comes into contact with the first connection portion 11 by a magnetic force of the first connection portion 11 formed of a permanent magnet. Accordingly, when a pressure of a fluid in the fluid chamber 24 becomes a positive pressure, the diaphragm 22 is displaced downward along the axis Y1, and such a displacement is transmitted to the diaphragm 12a through the second connection portion 23 and the first connection portion 11.

On the other hand, when a pressure of a fluid in the fluid chamber 24 becomes a negative pressure, the diaphragm 22 is displaced upward along the axis Y1. The second connection portion 23 is maintained in a state of being in contact with the first connection portion 11 by a magnetic force. Accordingly, when the diaphragm 22 and the second connection portion 23 are attracted to the fluid chamber 24 side, the first connection portion 11 and the diaphragm 12a are also attracted to the fluid chamber 24 side. For this reason, when the diaphragm 22 is displaced due to a negative pressure of a fluid in the fluid chamber 24, the diaphragm 12a joined to the first connection portion 11 is attracted to the fluid chamber 24 side so that a resistance value of the strain resistance changes to a value indicating a negative pressure together with the deformation of the diaphragm 12a.

The description is made with respect to the manner of operation and advantageous effects which the above-described pressure detection device 100 of this embodiment can acquire.

According to the pressure detection device 100 of this embodiment, the flow passage unit 20 is detachably mounted on the pressure detection unit 10 by the nut 30. Accordingly, to change a fluid which is made to flow through the flow passage 21a, the flow passage unit 20 which is already used is removed from the pressure detection unit 10, and a flow passage unit 20 which is unused can be newly mounted on the pressure detection unit 10.

With such a configuration, in changing a fluid which is made to flow through the flow passage 21a, it becomes unnecessary to perform a washing operation of the flow passage 21a, which requires a lot of time, so that smoothness of the operation can be improved. Further, a flow passage unit 20 which is unused can be newly used and hence, safety can be improved.

Further, according to the pressure detection device 100 of this embodiment, in a state where the flow passage unit 20 is mounted on the pressure detection unit 10 by the nut 30, the first connection portion 11 joined to the diaphragm 12a and the second connection portion 23 joined to the diaphragm 22 are disposed in a state where the connection portions are brought into contact with each other by a magnetic force. Accordingly, when a pressure of a fluid flowing through the flow passage 21a is a positive pressure, the second connection portion 23 joined to the diaphragm 22 is separated from the flow passage 21a side due to the pressure of the fluid, and the second connection portion 23 presses the first connection portion 11 to the diaphragm 12a. With such pressing, the pressure of the fluid is detected as a positive pressure by the strain resistance of the diaphragm 12a.

On the other hand, when a pressure of a fluid flowing through the flow passage 21a is a negative pressure, the second connection portion 23 joined to the diaphragm 22 is attracted to the flow passage 21a side due to the pressure of the fluid, and the second connection portion 23 attracts the first connection portion 11, which is connected to the second connection portion 23 by a magnetic force, to the flow passage 21a side. With such attraction, the pressure of the fluid is detected as a negative pressure by the strain resistance of the diaphragm 12a.

As described above, according to the pressure detection device 100 of this embodiment, it is possible to provide the pressure detection device 100 where smoothness and safety of an operation of changing a fluid which is made to flow through the flow passage 21a are improved, and a pressure of a fluid can be detected with accuracy even when the pressure of the fluid is a negative pressure.

Further, in the pressure detection device 100 of this embodiment, the first connection portion 11 is formed of a magnet, and the second connection portion 23 is formed of a magnetic body.

The flow passage unit 20, which is exchanged after being used, is formed of a magnetic body, which is relatively cheap. Accordingly, running cost can be reduced when the pressure detection device 100 is continuously used.

In the pressure detection device 100 of this embodiment, the end surface of the first connection portion 11 on the flow passage unit 20 side is formed into a planar shape, and the end surface of the second connection portion 23 on the pressure detection unit 10 side is formed into a spherical shape which projects toward the first connection portion 11.

With such a configuration, the first connection portion 11 and the second connection portion 23 are connected with each other only at one point of a spherical distal end of the first connection portion 11. Accordingly, a position where a pressure is transmitted between the first connection portion 11 and the second connection portion 23 is fixed to one point. Therefore, it is possible to prevent a problem that a position where a pressure is transmitted between the first connection portion 11 and the second connection portion 23 changes so that an error occurs in pressure detection value.

In the pressure detection device 100 of this embodiment, the pressure detection unit 10 includes the communication flow passage 12d which makes the inner space S1, defined by the diaphragm 22 and the diaphragm 12a, and the outer space S2, maintained at an atmospheric pressure, communicate with each other.

With such a configuration, the inner space S1 defined by the diaphragm 22 of the flow passage unit 20 and the diaphragm 12a of the pressure detection unit 10 is maintained at an atmospheric pressure. Accordingly, the diaphragm 12a can detect a pressure of a fluid with accuracy.

Second Embodiment

Next, a pressure detection device according to a second embodiment of the present disclosure is described with reference to drawings.

The second embodiment is a modification of the first embodiment. Hereinafter, unless otherwise specified below, the second embodiment is assumed equal to the first embodiment so that the same constitutional elements are given the same reference characters, and the description of such constitutional elements is omitted.

The pressure detection device of the second embodiment differs from the first embodiment with respect to a point that a positioning hole 11Aa is formed on a first connection portion 11A joined to the diaphragm 12a of the pressure detection unit 10.

Figure 6:
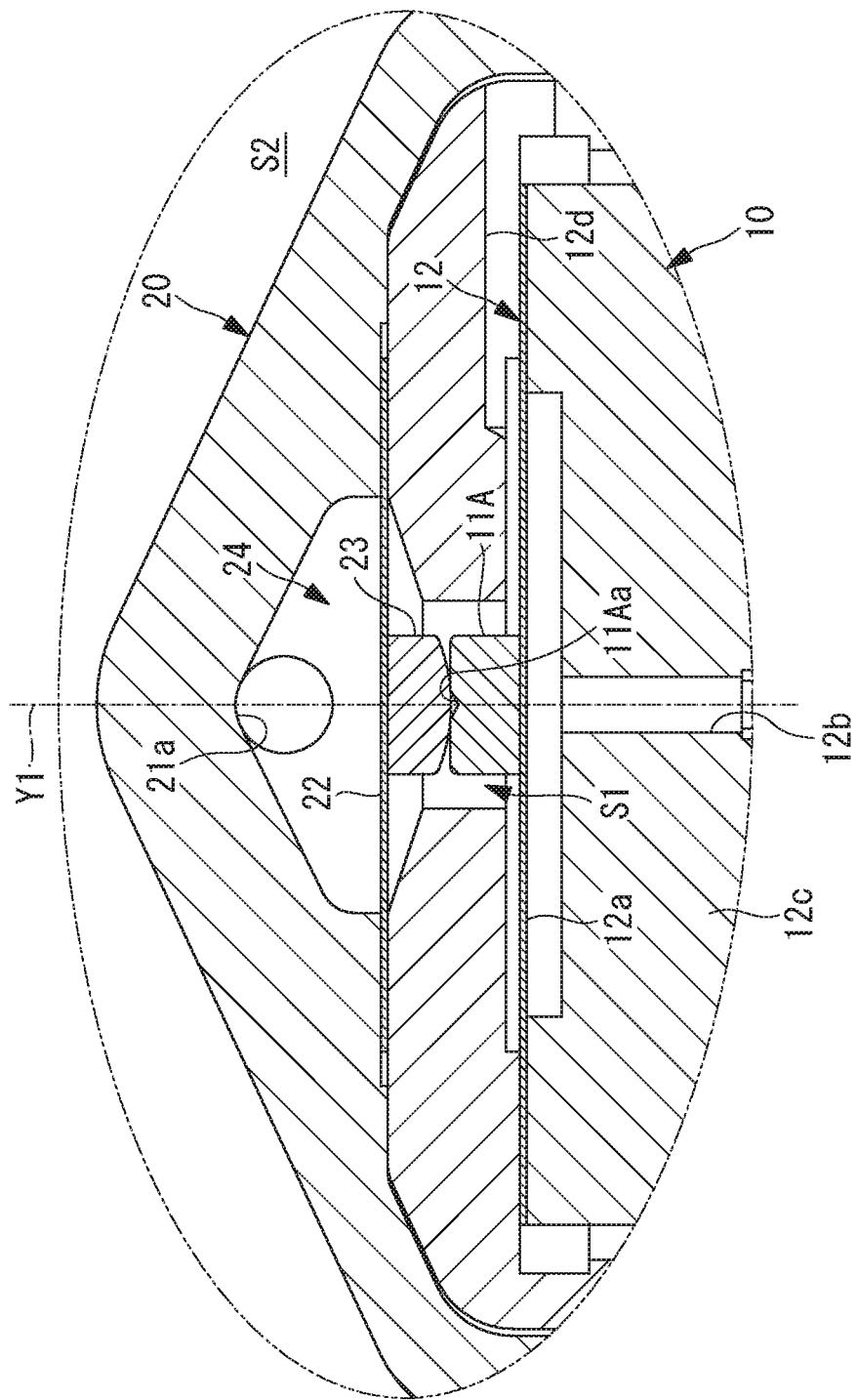
FIG. 6 is a partially enlarged view showing a pressure detection device of a second embodiment.

As shown in FIG. 6, an end surface of the first connection portion 11A on the flow passage unit 20 side is formed to have a planar shape disposed on a plane which is orthogonal to the axis Y1. Further, the positioning hole 11Aa is formed on an end surface of the first connection portion 11A on the flow passage unit 20 side.

The positioning hole 11Aa shown in FIG. 6 is a hole having a conical inner surface which is recessed downward. As shown in FIG. 6, the positioning hole 11Aa has a V shape which is recessed downward in longitudinal cross section taken along the axis Y1. In a state where the second connection portion 23 is brought into contact with the first connection portion 11A by a magnetic force, a center position of a spherical end surface of the second connection portion 23 is disposed at the position which agrees with the positioning hole 11Aa.

As shown in FIG. 6, a portion of the spherical end surface of the second connection portion 23 is accommodated in the positioning hole 11Aa at the center position which agrees with the axis Y1. Accordingly, even when an external force acts on the position where the first connection portion 11A and the second connection portion 23 are brought into contact with each other, the first connection portion 11A is hold such that the center position of the first connection portion 11A is not displaced from the position of the positioning hole 11Aa. With such a configuration, a pressure of a fluid which acts on the diaphragm 22 is transmitted to the diaphragm 12a from the position which agrees with the axis Y1 and hence, the diaphragm 12a can detect the pressure of the fluid with accuracy.

Third Embodiment

Next, a pressure detection device according to a third embodiment of the present disclosure is described with reference to drawings.

The third embodiment is a modification of the first embodiment. Hereinafter, unless otherwise specified below, the third embodiment is assumed equal to the first embodiment so that the same constitutional elements are given the same reference characters, and the description of such constitutional elements is omitted.

The pressure detection device of the third embodiment differs from the first embodiment with respect to a point that a second connection portion 23A which is joined to the diaphragm 22 of the flow passage unit 20 has an end surface on the pressure detection unit 10 side which is formed into a planar shape.

Figure 7:
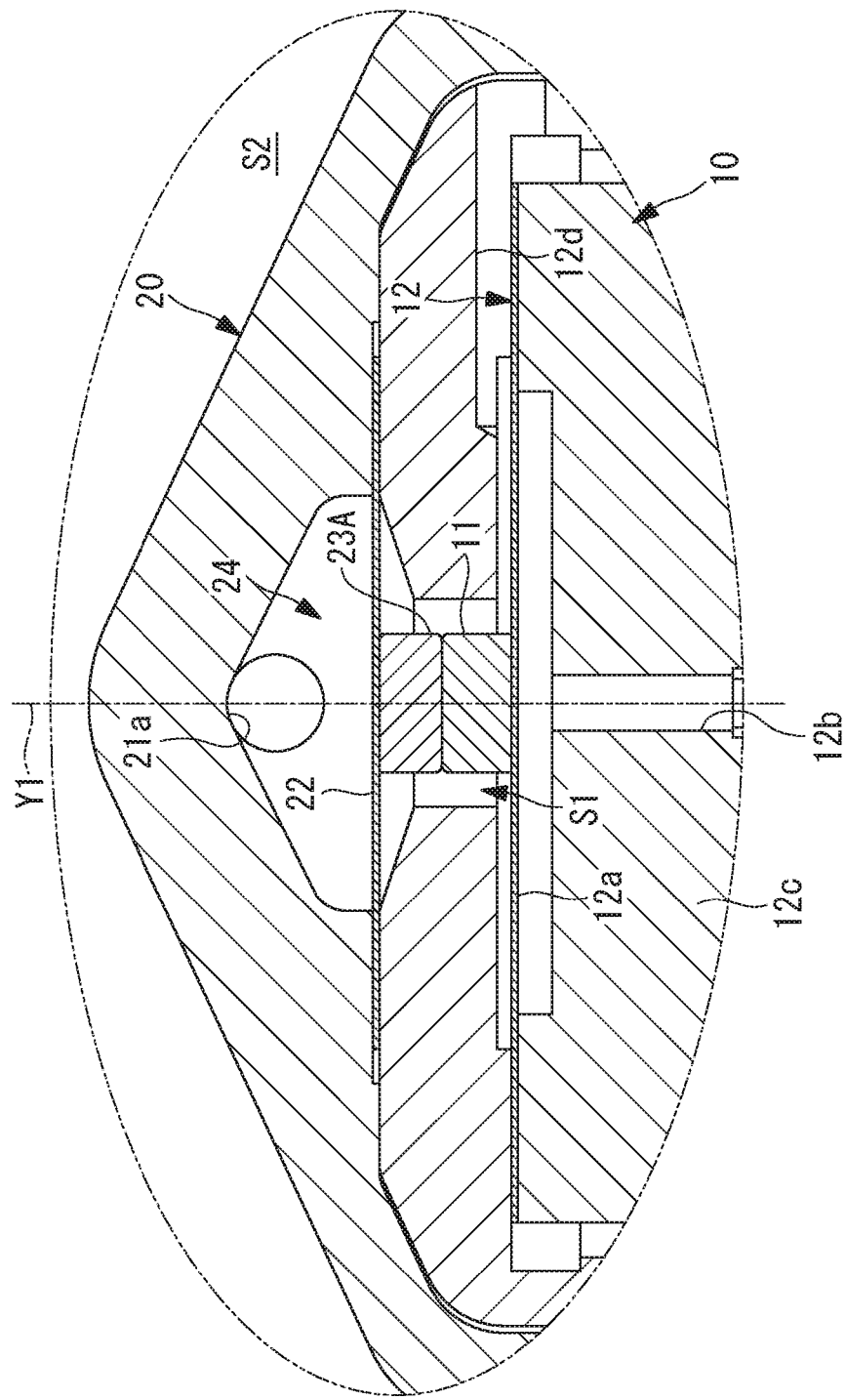
FIG. 7 is a partially enlarged view showing a pressure detection device of a third embodiment.

As shown in FIG. 7, the end surface of the second connection portion 23A on the pressure detection unit 10 side is formed to have a planar shape disposed on a plane orthogonal to the axis Y1. Further, an end surface of the first connection portion 11 on the flow passage unit 20 side is formed to have a planar shape disposed on a plane orthogonal to the axis Y1.

As described above, in the pressure detection device of the third embodiment, each of the end surface of the first connection portion 11 and the end surface of the second connection portion 23A, which opposedly face each other, has a planar shape. Accordingly, a contact area between the end surface of the first connection portion 11 and the end surface of the second connection portion 23A when these end surfaces come into contact with each other increases thus increasing a contact force, which is generated when the first connection portion 11 and the second connection portion 23A are brought into contact with each other by a magnetic force. Accordingly, when the pressure detection device of this embodiment and the pressure detection device of the first embodiment respectively adopt a permanent magnet having the same magnetic force, the pressure detection device of this embodiment can have a larger contact force between the first connection portion 11 and the second connection portion 23A.

By increasing a contact force between the first connection portion 11 and the second connection portion 23A which is joined to the diaphragm 22, an attracting force by which the second connection portion 23A attracts the first connection portion 11 increases when the diaphragm 22 and the second connection portion 23A move in the direction along which the diaphragm 22 and the second connection portion 23A are separated from the diaphragm 12a. For this reason, when the first connection portion 11 moves, it is possible to increase a distance where the first connection portion 11 can move while being in contact with the second connection portion 23A. Accordingly, the pressure detection device of this embodiment can increase a negative pressure measurement range compared to the pressure detection device of the first embodiment.

Fourth Embodiment

Next, a pressure detection device according to a fourth embodiment of the present disclosure is described with reference to drawings.

The fourth embodiment is a modification of the first embodiment. Hereinafter, unless otherwise specified below, the fourth embodiment is assumed equal to the first embodiment so that the same constitutional elements are given the same reference characters, and the description of such constitutional elements is omitted.

The pressure detection device of the fourth embodiment differs from the pressure detection device of the first embodiment with respect to a point that a second connection portion 23B is formed of a magnetic body 23Ba and a cover portion 23Bb made of a resin which accommodates the magnetic body 23Ba.

Figure 8:
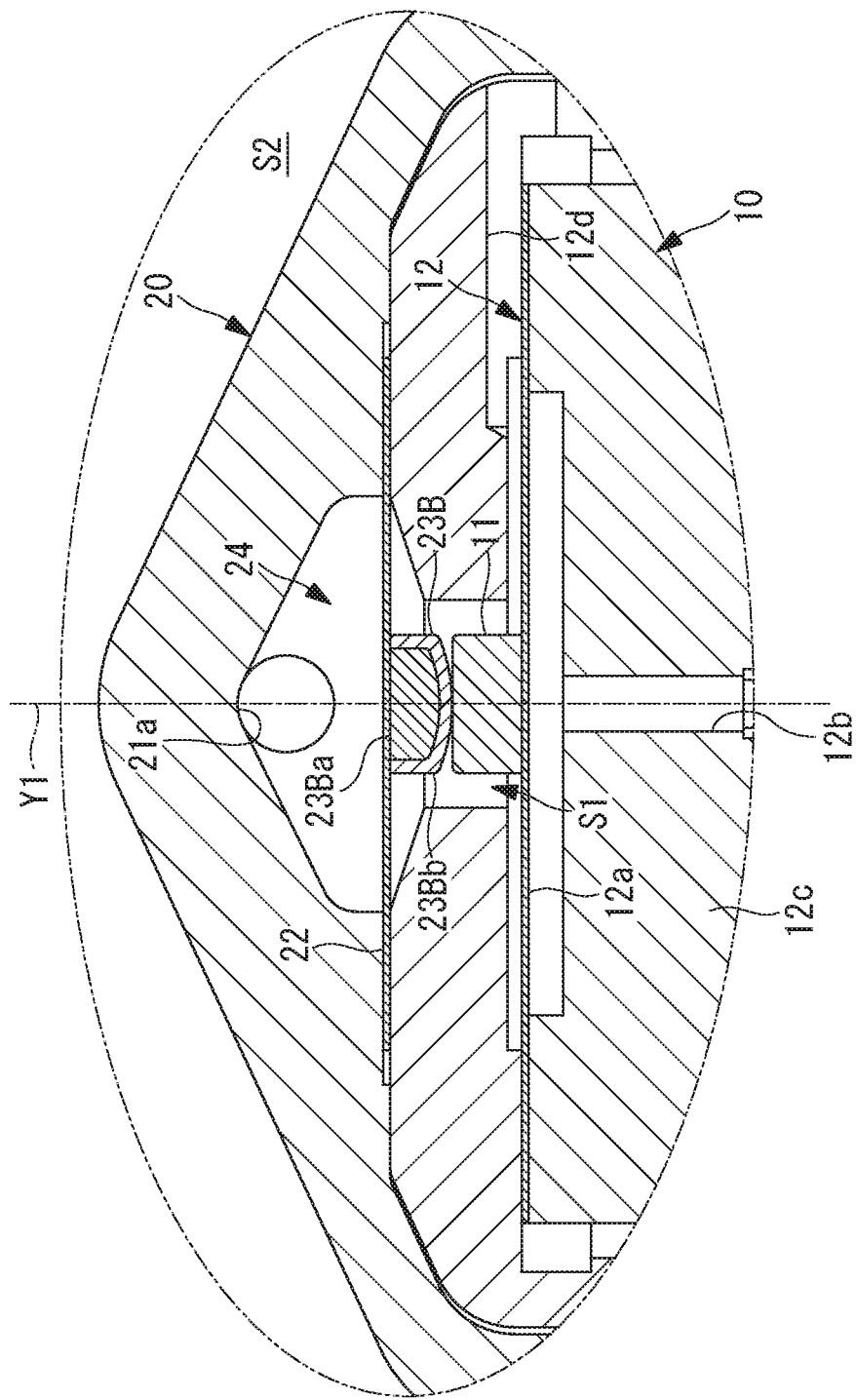
FIG. 8 is a partially enlarged view showing a pressure detection device of a fourth embodiment.

As shown in FIG. 8, the second connection portion 23B in this embodiment is formed of the magnetic body 23Ba and the cover portion 23Bb made of a resin which accommodates the magnetic body 23Ba. The magnetic body 23Ba is joined to the diaphragm 22 by an adhesive agent. The cover portion 23Bb is joined to the diaphragm 22 by an adhesive agent or by thermal welding.

With respect to the second connection portion 23B in this embodiment, the magnetic body 23Ba is protected by the cover portion 23Bb so as not to be exposed to the inner space S1. Accordingly, with the provision of the second connection portion 23B in this embodiment, it is possible to prevent problems such as a problem that the magnetic body 23Ba and the first connection portion 11 come into contact with each other thus causing wear of the magnetic body 23Ba and the first connection portion 11, or a problem that the magnetic body 23Ba is exposed to the inner space S1 thus causing corrosion of the magnetic body 23Ba.

The second connection portion 23B shown in FIG. 8 is formed such that the cover portion 23Bb covers only a periphery of the magnetic body 23Ba. However, another mode may be adopted. For example, as in the case of a second connection portion 23C shown in FIG. 9, it may be possible to adopt a modification where a cover portion 23Cb made of a resin covers not only a periphery of a magnetic body 23Ca but also an entire end surface of the diaphragm 22 on the pressure detection unit 10 side. According to this modification, the entire end surface of the diaphragm 22 on the pressure detection unit 10 side is covered by the cover portion 23Cb and hence, the diaphragm 22 can be protected. Further, it is possible to prevent a problem that the magnetic body 23Ca is peeled off from the diaphragm 22.

Figure 9:
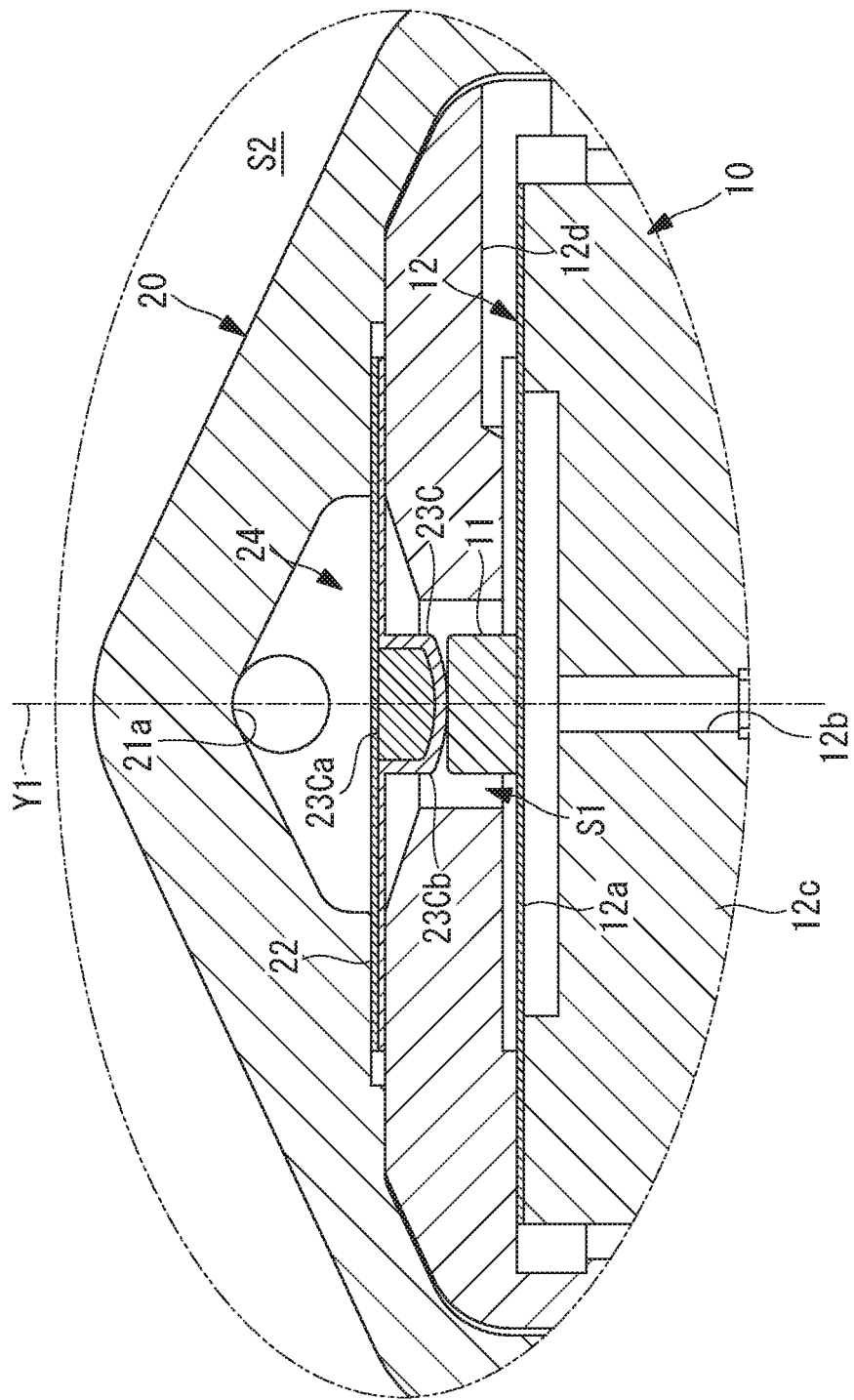
FIG. 9 is a partially enlarged view showing a modification of the pressure detection device of the fourth embodiment.

It is also possible to adopt another modification where, in addition to the configuration of the second connection portion 23C shown in FIG. 9, a first connection portion 11B is formed of a permanent magnet 11Ba and a cover portion 11Bb made of a resin which accommodates the permanent magnet 11Ba.

Figure 10:
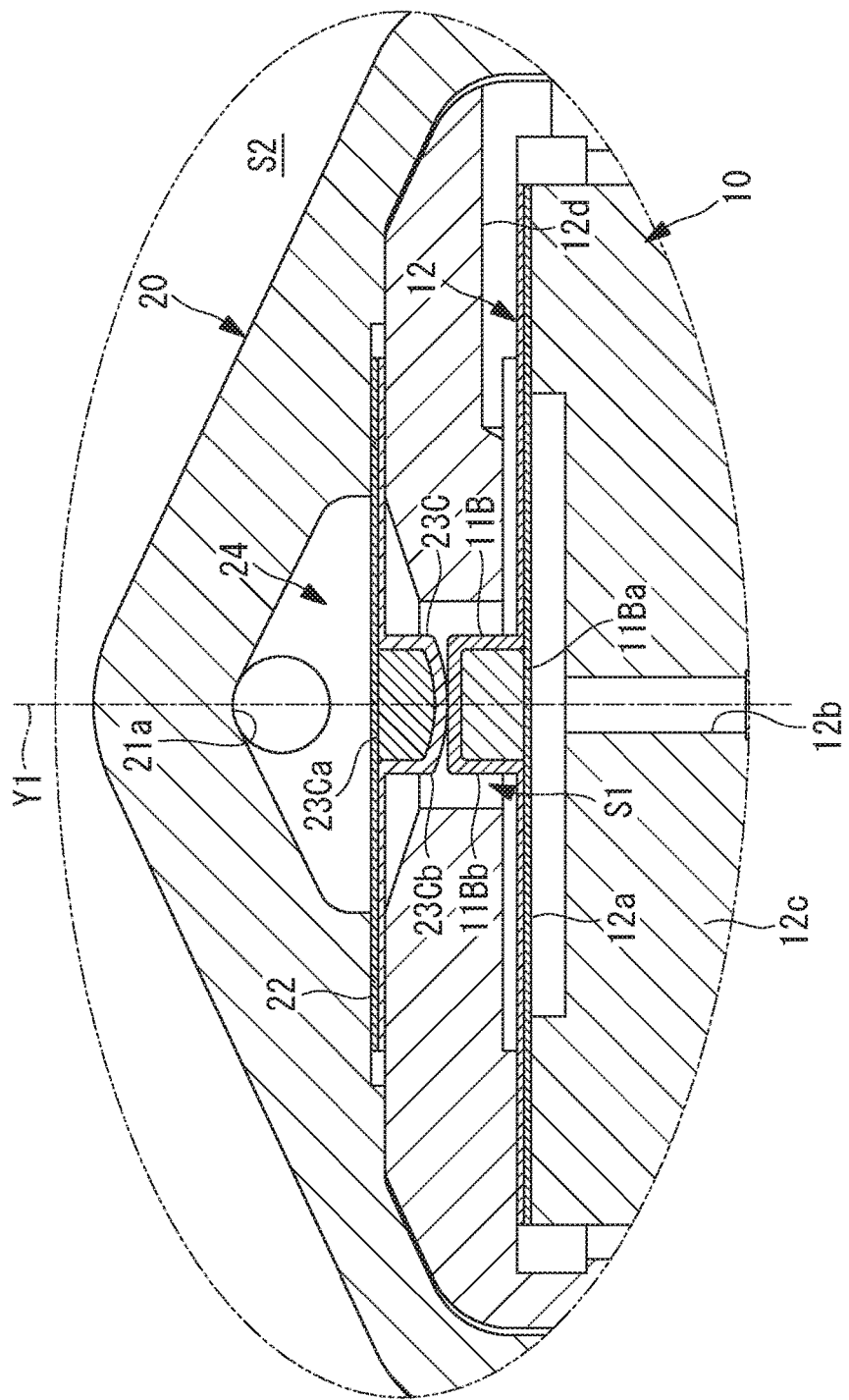
FIG. 10 is a partially enlarged view showing another modification of the pressure detection device of the fourth embodiment.

As shown in FIG. 10, with respect to the first connection portion 11B in another modification, the permanent magnet 11Ba is protected by the cover portion 11Bb so as not to be exposed to the inner space S1. Accordingly, with the provision of the first connection portion 11B in this modification, it is possible to prevent problems such as a problem that the permanent magnet 11Ba and the second connection portion 23C come into contact with each other thus causing wear of the permanent magnet 11Ba and the second connection portion 23C, or a problem that the permanent magnet 11Ba is exposed to the inner space S1 thus causing corrosion of the permanent magnet 11Ba. Further, the entire end surface of the diaphragm 12a on the flow passage unit 20 side is covered by the cover portion 11Bb and hence, the diaphragm 12a can be protected. It is also possible to prevent a problem that the permanent magnet 11Ba is peeled off from the diaphragm 12a.

Fifth Embodiment

Next, a pressure detection device according to a fifth embodiment of the present disclosure is described with reference to drawings.

The fifth embodiment is a modification of the first embodiment. Hereinafter, unless otherwise specified below, the fifth embodiment is assumed equal to the first embodiment so that the same constitutional elements are given the same reference characters, and the description of such constitutional elements is omitted.

The pressure detection device of the fifth embodiment differs from the pressure detection device of the first embodiment with respect to a point that a second connection portion 23D is integrally formed with the diaphragm 22 by insert molding.

Figure 11:
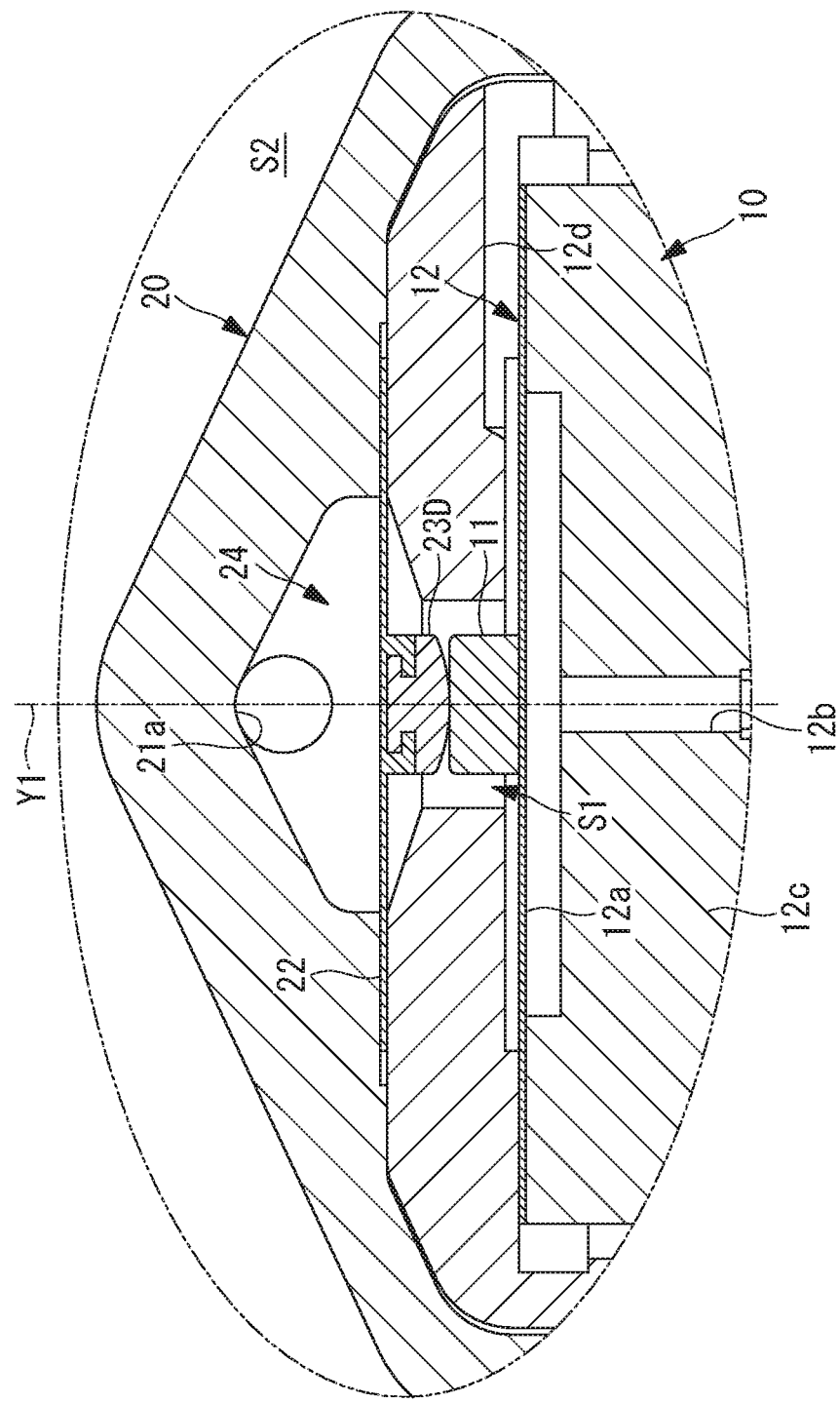
FIG. 11 is a partially enlarged view showing a pressure detection device of a fifth embodiment.

As shown in FIG. 11, in the pressure detection device of this embodiment, a portion of the second connection portion 23D on the flow passage 21a side is formed into a shape where an upper end portion has a large diameter about the axis Y1, and a portion below the upper end portion has a smaller diameter about the axis Y1 than the upper end portion. Further, the second connection portion 23D is integrally formed with the diaphragm 22 made of a resin material by insert molding.

In the pressure detection device of this embodiment, the second connection portion 23D is integrally formed with the diaphragm 22 so that it is unnecessary to join the second connection portion 23D to the diaphragm 22 by an adhesive agent or by thermal welding. Accordingly, compared to the case where the second connection portion 23D is joined to the diaphragm 22, it is possible to reduce a manufacturing cost in manufacturing a pressure detection device.

Sixth Embodiment

Next, a pressure detection device according to a sixth embodiment of the present disclosure is described with reference to drawings.

The sixth embodiment is a modification of the first embodiment. Hereinafter, unless otherwise specified below, the sixth embodiment is assumed equal to the first embodiment so that the same constitutional elements are given the same reference characters, and the description of such constitutional elements is omitted.

The pressure detection device 100 of the first embodiment is configured such that the first connection portion 11 is joined to the surface of the diaphragm 12a which is in contact with the inner space S1. On the other hand, in the pressure detection device of this embodiment, the first connection portion 11B is joined to a surface of the diaphragm 12a which is not in contact with the inner space S1.

Figure 12:
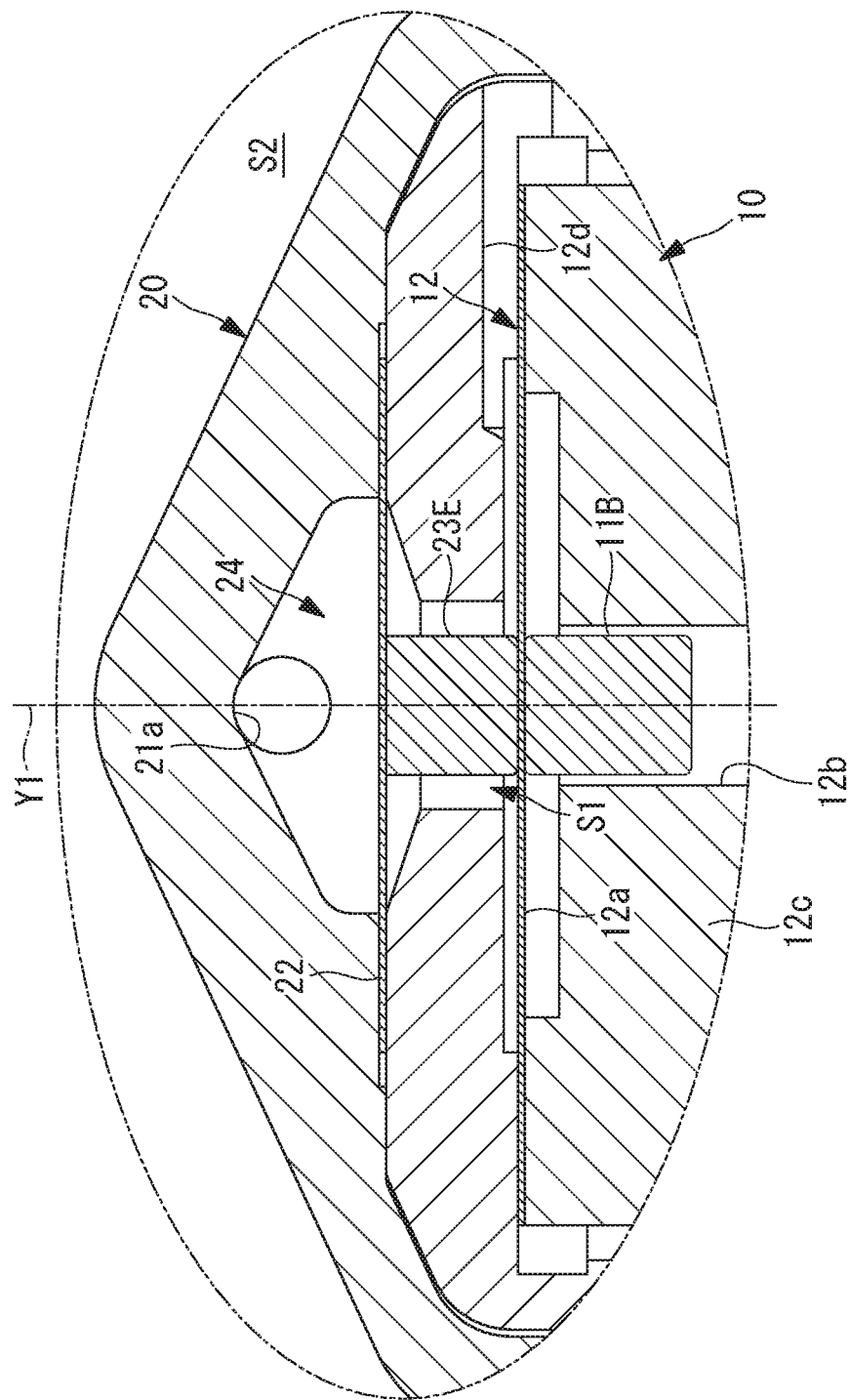
FIG. 12 is a partially enlarged view showing a pressure detection device of a sixth embodiment.

As shown in FIG. 12, in the pressure detection device of this embodiment, the first connection portion 11B formed into a cylindrical shape using a permanent magnet is joined to the surface of the diaphragm 12a which is not in contact with the inner space S1. The through hole 12b is formed in the surface of the diaphragm 12a which is not in contact with the inner space S1, and the through hole 12b maintains a pressure applied to the surface of the diaphragm 12a at an atmospheric pressure. In this embodiment, the first connection portion 11B is disposed in the through hole 12b so as to prevent the inner space S1 from increasing.

In the pressure detection device of this embodiment, the first connection portion 11B is joined to the surface of the diaphragm 12a on the side which is not in contact with the inner space S1. Further, in the pressure detection device of this embodiment, a second connection portion 23E is joined to the surface of the diaphragm 22 on the side which is in contact with the inner space S1. With such a configuration, in removing the flow passage unit 20 from the pressure detection unit 10, a magnetic force in the direction that the first connection portion 11B approaches the diaphragm 12a acts on a portion where the first connection portion 11B and the diaphragm 12a are joined to each other. This is because the first connection portion 11B generates a magnetic force of attracting the second connection portion 23E. Accordingly, compared to the case of the first embodiment where the first connection portion is joined to the surface of the diaphragm 12a on the side which is in contact with the inner space S1, it is possible to prevent, by the action of a magnetic force, a problem that the first connection portion is peeled off from the diaphragm 12a.

Further, the first connection portion 11B is disposed in a space isolated from the inner space S1 by the diaphragm 12a. With such a configuration, there is no possibility that a manipulator inadvertently comes into contact with the portion where the first connection portion 11B and the diaphragm 12a are joined to each other. Accordingly, it is possible to prevent a problem that the first connection portion 11B is peeled off from the diaphragm 12a due to carelessness of the manipulator.

Another Embodiment

In the description made heretofore, the flow passage unit 20 includes the flow passage body 21 and the diaphragm 22 joined to the flow passage body 21. However, another mode may be adopted.

For example, the flow passage unit 20 may be formed such that the flow passage body 21 and the diaphragm 22 are formed into one integral body using a single material.

The invention claimed is:

1. A pressure detection device comprising:
a pressure detection unit configured to detect a pressure transmitted to a pressure detecting portion;
a flow passage unit in which a flow passage for introducing a fluid is formed; and
a mounting mechanism configured to detachably mount the flow passage unit on the pressure detection unit, wherein
the pressure detection unit includes:
a pressure sensor including the pressure detecting portion; and
a first connection portion joined to the pressure detecting portion,
the flow passage unit includes:
a pressure receiving portion configured to be displaced by receiving a pressure of the fluid flowing through the flow passage; and
a second connection portion joined to the pressure receiving portion,
one of the first connection portion and the second connection portion is formed of a magnet, and the other of the first connection portion and the second connection portion is formed of a magnet or a magnetic body,
the mounting mechanism comprises a first fastening member mounted on the flow passage unit and a second fastening member mounted on the pressure detection unit,
the first connection portion that is joined to the pressure detecting portion of the pressure detection unit and the second connection portion that is joined to the pressure receiving portion of the flow passage unit are brought into contact with each other by fastening the first fastening member to the second fastening member, and
in a state where the flow passage unit is mounted on the pressure detection unit by the mounting mechanism, the first connection portion and the second connection portion are disposed in a state where the first connection portion and the second connection portion are attracted to and brought into contact with each other by a magnetic force,
the second connection portion is disposed in an inner space defined by the pressure receiving portion and the pressure detecting portion,
the first connection portion is joined to a surface of the pressure detecting portion which is not in contact with the inner space, and
in the state where the flow passage unit is mounted on the pressure detection unit by the mounting mechanism, the first connection portion and the second connection portion are disposed in the state where the first connection portion and the second connection portion are attracted to each other by the magnetic force with the pressure detecting portion interposed between the first connection portion and the second connection portion.

2. The pressure detection device according to claim 1, wherein the first connection portion is formed of the magnet, and the second connection portion is formed of the magnetic body.

3. The pressure detection device according to claim 1, wherein an end surface of the first connection portion on a side of the flow passage unit is formed to have a planar shape, and
an end surface of the second connection portion on a side of the pressure detection unit is formed to have a spherical shape which projects toward the first connection portion.

4. The pressure detection device according to claim 2, wherein an end surface of the first connection portion on a flow passage unit side is formed to have a planar shape, and
an end surface of the second connection portion on a pressure detection unit side is formed to have a spherical shape which projects toward the first connection portion.

5. The pressure detection device according to claim 1, wherein the pressure detection unit has a communication flow passage configured to make an inner space defined by the pressure receiving portion and the pressure detecting portion and an outer space maintained at an atmospheric pressure communicate with each other.

6. The pressure detection device according to claim 1, wherein the pressure sensor outputs a pressure signal which corresponds to a deformation of the pressure detecting portion according to a change of a pressure transmitted to the pressure detecting portion.

7. The pressure detection device according to claim 1, wherein in the state where the flow passage unit is mounted on the pressure detection unit by the mounting mechanism, the first connection portion and the second connection portion are disposed in the state where the first connection portion and the second connection portion are attracted to and brought into direct contact with each other by the magnetic force.

8. The pressure detection device according to claim 1, wherein in the state where the flow passage unit is mounted on the pressure detection unit by the mounting mechanism, the first connection portion and the second connection portion are disposed in the state where the first connection portion and the second connection portion are attracted to and brought into contact with each other, via at least one cover portion, by the magnetic force.

9. A pressure detection device comprising:
a pressure detection unit configured to detect a pressure transmitted to a pressure detecting portion;
a flow passage unit in which a flow passage for introducing a fluid is formed; and
a mounting mechanism configured to detachably mount the flow passage unit on the pressure detection unit, wherein
the pressure detection unit includes:
a pressure sensor including the pressure detecting portion; and
a first connection portion joined to the pressure detecting portion,
the flow passage unit includes:
a pressure receiving portion configured to be displaced by receiving a pressure of the fluid flowing through the flow passage; and
a second connection portion joined to the pressure receiving portion,
one of the first connection portion and the second connection portion is formed of a magnet, and the other of the first connection portion and the second connection portion is formed of a magnet or a magnetic body, in a state where the flow passage unit is mounted on the pressure detection unit by the mounting mechanism, the first connection portion and the second connection portion are disposed in a state where the first connection portion and the second connection portion are attracted to each other by a magnetic force, the second connection portion is disposed in an inner space defined by the pressure receiving portion and the pressure detecting portion, the first connection portion is joined to a surface of the pressure detecting portion which is not in contact with the inner space, and in the state where the flow passage unit is mounted on the pressure detection unit by the mounting mechanism, the first connection portion and the second connection portion are disposed in the state where the first connection portion and the second connection portion are attracted to each other by the magnetic force with the pressure detecting portion interposed between the first connection portion and the second connection portion.

* * * * *